United States Patent [19]
Dawson

[11] Patent Number: 5,891,213
[45] Date of Patent: Apr. 6, 1999

[54] ON-LINE PRODUCTION CONTROL OF CAST IRONS BY MEASURING THE SURFACE TENSION OF THE BASE TREATED IRON

[75] Inventor: Steve Dawson, Pully, Switzerland

[73] Assignee: Sintercast AB, Sweden

[21] Appl. No.: 952,768

[22] PCT Filed: May 21, 1996

[86] PCT No.: PCT/SE96/00659

§ 371 Date: Nov. 28, 1997

§ 102(e) Date: Nov. 28, 1997

[87] PCT Pub. No.: WO96/38595

PCT Pub. Date: Dec. 5, 1996

[30] Foreign Application Priority Data

May 29, 1995 [SE] Sweden ................................. 9501960

[51] Int. Cl.[6] .......................... C22C 33/08; G01N 13/02; G01N 33/20
[52] U.S. Cl. .............................. 75/377; 164/4.1; 164/57.1
[58] Field of Search ..................... 164/4.1, 57.1, 164/58.1, 55.1, 56.1; 75/377; 420/29, 30; 266/79

[56] References Cited

U.S. PATENT DOCUMENTS

| | | | |
|---|---|---|---|
| 3,284,192 | 11/1966 | Larson et al. | 75/377 X |
| 3,765,227 | 10/1973 | Campbell et al. | |
| 4,246,026 | 1/1981 | Stefanescu et al. | 75/377 X |
| 4,449,700 | 5/1984 | Erpelding | 266/79 |
| 5,305,815 | 4/1994 | Pan Ping et al. | 164/4.1 |
| 5,615,730 | 4/1997 | Hiraoka et al. | 164/4.1 |

FOREIGN PATENT DOCUMENTS

| | | |
|---|---|---|
| 40 35 768 | 5/1992 | Germany . |
| WO86/01755 | 3/1986 | WIPO . |

OTHER PUBLICATIONS

Kozakevitch et al: "Surface Tension of Pure Liquid Iron, Cobalt, and Nickel at 1550° C.", Journal of the Iron and Steel Institute, Jun. 1957, pp. 167–173.

Mizina et al: "Surface tension of complex inoculants and their efficency for smelting cast iron", Dialog Information Services, file 21, Metadex, Dialog accession no. 1848281, Metadex Accession No. 199501–45–0034, Rasplavy, vol. 1, pp. 88–91, Jan.–Feb. 1994, (abstract only).

Kul'Bovskii: "Factors Influencing Graphite Particle Form in Cast Iron", Soviet Castings Technolgy (Now: Russian Castings Technology)) See also: Liteinoe Proizvodstavo). Dialog Information Services, File 32, Metadex, Dialog accession No. 1814414, Metadex accession No. 199402–51–0166, vol. 2, pp. 11–12, 1991 (abstract only).

Herfurth: "Investigation of the effect of various allloying additions on the surface tension of liquid cast iron to establish correlations between surface tension and the formation of various forms of graphite", Freiberger Forsch B 105, 1966, pp. 267–310, see pp. 281–288 and pp. 299–307 (abstract).

(List continued on next page.)

*Primary Examiner*—J. Reed Batten, Jr.
*Attorney, Agent, or Firm*—Pillsbury Madison & Sutro, LLP

[57] ABSTRACT

The surface tension of a sample quantity of molten iron from a batch of molten iron is determined and compared with the surface tension of the sample with the surface tensions of batches of molten iron that are known to solidify as respective different forms of cast iron. The surface tension of the molten iron sample is determined by adding the sample to a sample cup, submerging a device for introducing a noble gas into the molten iron of the sample, positioning a piezoelectric transducer at the bottom of the sample cup, administrating the noble gas at a constant rate through the device, measuring the temperature of the sample, and monitoring vibrations in the molten iron of the sample by recording signals from the transducer.

6 Claims, 2 Drawing Sheets

OTHER PUBLICATIONS

Nosov et al: The Surface Tension and Thermo-physical Properties of Cast Irons Modified With Magnesium, Yttrium, Gadolinium, and Zicronium, Fiz–Khim. Issled. Metall. Protessov, vol. 10, pp. 60–63, 1982, Dialog Information Serices, File 32, Metadex, Dialog Accession No. 888163, Metadex Accession No. 84–320362 (Abstract).

Aleksandrov et al: "A study of Graphite Formation in Cast Iron: Methods of Controlling Cast Iron Properties at the Casting Stage", Fonderia Ital., 27 (4) 103–107, Apr. 1978 (abstract).

ON-LINE PRODUCTION CONTROL OF CAST IRONS BY MEASURING THE SURFACE TENSION OF THE BASE TREATED IRON

This application is the national phase of international application PCT/SE96/00659, filed May 21, 1996 which designated the U.S.

BACKGROUND OF THE INVENTION

The present invention relates to a new method for predicting the nucleation and growth of graphite crystals during the solidification of cast irons.

WO-A1-86/01755 relates to such a method. A sample from a bath of molten iron is permitted to solidify during 0.5 to 10 minutes. The temperature is recorded simultaneously by two temperature responsive means, one of which is placed in the center of the sample and the other in the immediate vicinity of the vessel wall. The number and shape of the graphite particles which constitute the graphite phase is assessed in relation to known reference values by aid of recorded values of supercooling at the vessel wall, the recalescence at the vessel wall, the difference between the temperature at the vessel wall and at the center of the vessel and the maximum slope of the temperature time curve during the period of constant eutectic growth temperature at the center. The method can be used for calculating the amounts of inoculants and graphite structure modifiers that have to be added or removed in order to obtain a cast iron comprising a desired form of cast iron, such as flaky graphite iron, compacted graphite iron (CGI) and spheroidal graphite iron (SGI).

The method according to WO-A1-86/01755 produces excellent results, but it also has some drawbacks. The amount of time required for the determination, up to 10 minutes may be rather high, and the measurement per se is also rather complicated. Hence, there is a need for a quick, simple and reliable method for predicting the nucleation and growth of graphite crystals during the solidification of cast irons.

SUMMARY OF THE INVENTION

The aforesaid problem in connection with producing cast irons having a certain desired morphology of graphite crystals and containing graphite shape modifiers and/or inoculants, is solved by a method in accordance with the invention, according to which:

a) a sample quantity of the molten iron is taken from the batch of molten iron;
b) the surface tension of the sample is determined; and finally
c) the surface tension of the sample is compared with the surface tensions of batches of molten iron that are known to solidify as different forms of cast iron.

BRIEF DESCRIPTION OF THE DRAWINGS

The invention will now be described with reference to the accompanying drawings according to which.

DETAILED DESCRIPTION OF PREFERRED EMBODIMENTS OF THE INVENTION

Figure 1:
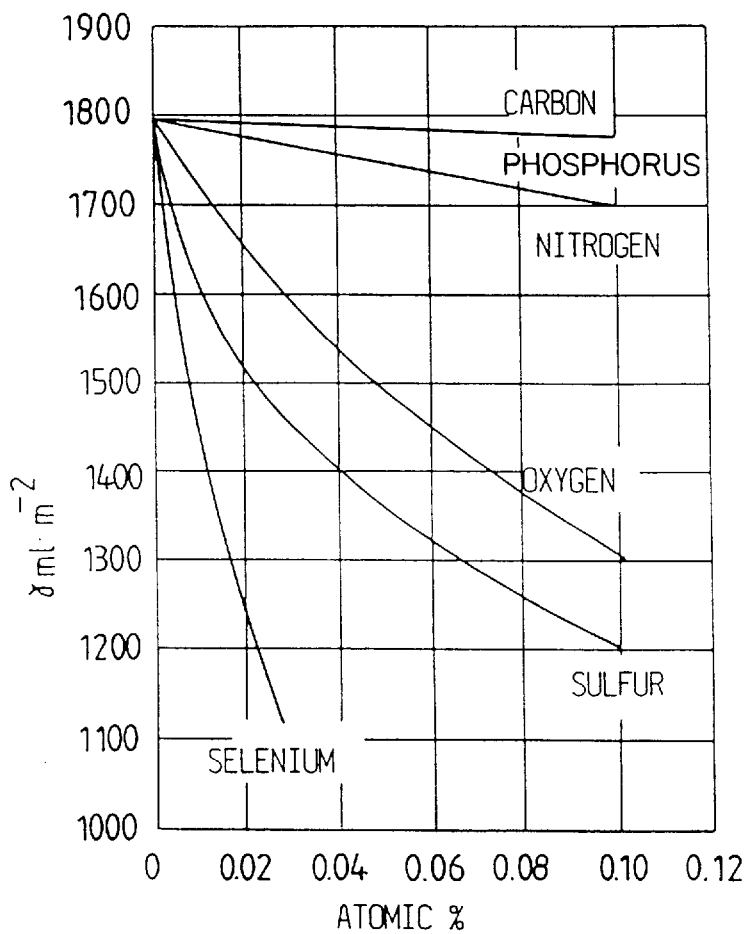
FIG. 1 is a graphic representation of the surface tension of liquid iron as a function of the concentration of the highly surface active elements, oxygen, sulfur and selenium, and standard components of cast irons which are less surface active such as nitrogen, phosphorus and carbon.

The method according to the present invention is based on an accurate measurement of the surface tension of the liquid iron following base treatment with inoculants and graphite shape modifiers such as magnesium. As is shown in FIG. 1, it is well-known (See P. Kzakevitch and G. Urbain: J. of the Iron and Steel Institute (JISI), Vol. 186, 1957, pp. 167–170.) that the surface tension of liquid iron changes with varying contents of surface active elements such as sulfur and oxygen. As the concentration of these elements increases, the surface tension of liquid iron decreases thus allowing the formation of elongated graphite crystals with a high surface area-to-volume ratio such as is found in conventional grey cast irons. With lower concentrations of sulfur and oxygen, the surface tension of the liquid iron increases thus favoring the formation of spheroidal graphite crystals which have a minimized surface area-to-volume ratio. Compacted graphite crystals, which are arguably a three-dimensionally growth-distored form of flake graphite morphology, are known to grow preferentially at intermediate values of liquid iron surface tension.

While several theories regarding the growth mechanism and ultimate shape of graphite have been proposed, the common denominator in all theories is that they are invariably linked to the so-called dissolved or active sulfur and oxygen contents of the molten iron, which in-turn determines the surface tension of the molten iron. Therefore, by monitoring the surface tension of the molten iron, it will be possible to predict the ultimate shape of the graphite crystals immediately after base treatment so that corrective amounts of magnesium and inoculant may be added to the melt before it is cast into molds and thus minimize the proportion of unacceptable or out-of-specification castings.

Figure 2A:
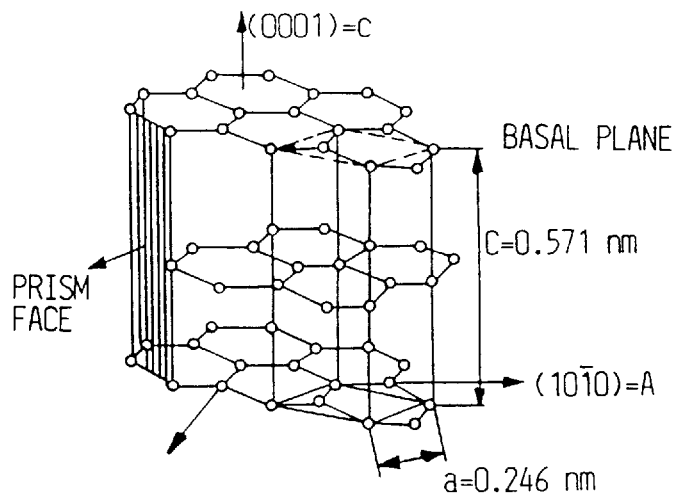
FIGS. 2A and 2B illustrate the atomic structure of graphite and defines the A-axis and C-axis directions of growth of graphite crystals.
Figure 2B:
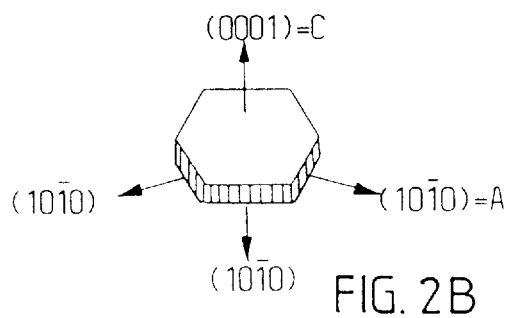

One such theory recognises that the atomic lattice of graphite is an hexagonal close-packed structure (FIG. 2) with the possibility to grow in either the A-axis prism face direction (as in grey flake iron) or in the C-axis basal plane direction (as in spheroidal graphite iron). Physical measurements of liquid iron surface tension, which are disclosed in Table I (See H. Geilenberg: Recent Research on Cast Iron, H. D. Merchant (Ed), Gordon and Breach, 1968, pp. 195–210.), clearly shows that, when the sulfur and oxygen content of the iron is high (as in grey cast iron), the surface tension at the interface between the A-axis and the molten iron is lower than that between the C-axis and the liquid iron. Therefore, growth is favored in the A-direction thus producing elongated graphite flakes. Conversely, in the absence of dissolved oxygen and sulfur, while the graphite/iron surface tension is higher than when oxygen and sulfur are present as shown in FIG. 1, the surface tension at the interface between the A-axis and the molten iron is higher than that between the C-axis and the molten iron. Therefore, growth is favored in the relatively low energy C-direction thus producing spheroidal graphite crystals.

Another common theory of graphite growth mechanisms suggests that sulfur and oxygen tend to adsorb onto the A-axis prism faces thus increasing the atomic density and roughness of the A-face which improves the rate of carbon atom deposition of the A-face. Ultimately, the preferential addition of carbon atoms to the A-face results in the formation of flake graphite. By the same theory, when magnesium or cerium or lanthanum or other known graphite shape-modifying elements are added to the liquid iron, they react with dissolved oxygen and sulfur thus "scavenging" or cleaning the A-faces of the graphite lattice. Under these circumstances the C-face or basal plane of the graphite lattice has a higher atomic density and carbon atoms preferentially deposit on it resulting in C-axis growth and the ultimate formation of spheroidal graphite crystals.

Regardless of the exact growth mechanism, for which considerable debate has been conducted, it is clear that the presence of sulfur and oxygen are of paramount importance. The novel contribution of the present invention is to accurately measure the surface tension of the molten iron, after the addition of magnesium and inoculant (which consumes dissolved oxygen and sulfur atoms through chemical reaction), to determine if the surface tension is within an acceptable range for the stable growth of compacted graphite iron, or equally, for the successful production of high quality spheroidal graphite iron. The results of the surface tension analysis will allow for the inoculant and/or magnesium contents of the base treated iron to be corrected prior to casting to ensure an optimal solidification behavior of the melt. It must also be noted that the present invention may also be useful for the production of conventional grey cast irons. As described previously, a certain amount of oxygen and/or sulfur must be present at the A-face to promote the growth of flakes. An accurate measurement of surface tension will allow the skilled foundry worker to determine the need for additional inoculation, or alternatively, oxygen sources. This is particularly true when it is realized that selenium and tellurium are even more surface active in molten iron than are oxygen and sulfur. Given the inevitable deterioration of ferrous metal charge materials in the future, it may become essential to measure the accumulation of these elements in the iron and take corrective actions in real-time, by monitoring surface tension prior to casting.

A very important advantage of the present invention is that the results are available very quickly. Unlike known thermal analysis control methods, such as the one disclosed in WO-A1-86/01755, it is not necessary for the iron sample to solidify. The analysis can be fully conducted with the first bubble formation, and verification can be achieved through the surface tension analysis of subsequent bubbles. The entire analysis from taking a sample of the molten iron until issuing a prediction of graphite morphology can require less than one minute. Upon completion of the analysis, corrective actions are prescribed to either increase or decrease the degree of inoculation and magnesium modification. The optimised iron can then be cast with conventional foundry techniques.

The invention will now be described with respect to the following examples of preferred embodiments. However, these examples are only given for the purpose of illustration, and are not intended to limit the scope of the invention.

Figure 3:
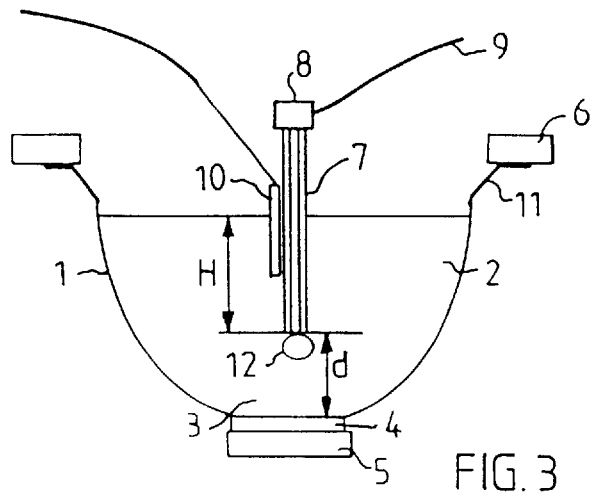
FIG. 3 is a schematic illustration of the measuring equipment.

The surface tension analysis of the present invention can be performed by using equipment as illustrated in FIG. 3. The analysis equipment basically comprises a sample cup (1). A sample cup (1) made of steel is preferred to conventional high temperature ceramic crucibles in order to effectively transmit vibrations originating from within the melt. The liquid iron sample (2), which is filled into the cup can be of any size greater than approximately 100 g, but is preferably in the range of 200–1000 g. A noble gas (9), such as helium, neon, argon, krypton or xenon is then transported through a valve (8) and a submerged refractory lance (7) and subsequently bubbled through the liquid iron sample (2). A thermocouple (10) is also submerged in the liquid iron sample (2). The thermocouple (10) may be an integrated part of the refractory lance (7), but can also be independent of the gas lance. Finally, a piezoelectric transducer (4) is attached to the wall of the steel cup (1) to monitor the vibration behaviour of the gas bubbles which form at the tip of the injection lance (7). The transducer (4) is inexpensive and can either be re-usable or disposable. The actual contact time for the transducer (4) to the steel cup (1) is less than fifteen seconds which allows the transducer (4) to stay well below its Currie point (for example 190° –350° C. for lead circonate titanate, 400° C. for lead metaniobate; or 1210° C. for lithium niobate). The base (3) of the sample cup is flat in order to ensure good physical contact between the sample cup (1) and the transducer (4). A retraction device (5) makes it possible adjust the vertical position of the transducer (4) with respect to the sample cup (1).

Operationally, once the sample cup (1) has been filled with molten iron (2), a clamping device (6) is applied around around the top perimeter (11) of the cup to ensure contact between the cup and the transducer and also to eliminate external noise vibrations. The gas flow is then initiated and the transducer (4) is raised to make direct contact with the flattened base (3) of the sample cup (1). The gas flow is adjusted in a manner which allows the bubble (12) to fully form at the tip of the lance while no other bubbles are present in the molten iron to produce extraneous noise.

The growth rate of the bubble and its vibration amplitude and frequency is a function of the gas pressure and the distance H between surface of the molten iron and the lance tip (amount of ferrostatic head) and most importantly, the surface tension of the liquid iron. By controlling the pressure and accepting that variations in ferrostatic head are sufficiently small to be neglected, the vibration behavior of the single bubble (12) at the tip of the lance (7) can be quantified by the transducer. Then, with a knowledge of the gas pressure, the distance d from the tip of the lance (7) to the flattened base (3) of the sample cup (1), and the temperature of the liquid iron as obtained from the thermocouple (10), one can readily deduce the surface tension by evaluating the vibration frequency spectrum and comparing with known reference samples and thus predicting the ultimate shape of graphite particles in the final casting.

TABLE I

Interfacial tension between liquid iron and graphite as a function of sulfur and oxygen contents, and the growth plane of the graphite lattice.

| Crystal Plane | Surface tension (mJ/m$^2$) | |
| --- | --- | --- |
| | with O & S | no O & S |
| Prism (A) | 845 | 1720 |
| Basal (C) | 1270 | 1460 |

I claim:

1. A method for predicting nucleation and growth of graphite crystals during solidification of cast iron from a batch of molten iron, comprising the steps of:
    (a) taking a sample from the batch of molten iron;
    (b) determining the surface tension of said sample, by:
        i. adding said sample to a sample cup which has a bottom;
        ii. submerging into said sample in said sample cup a device for introducing a noble gas into the molten iron of said sample;
        iii. positioning a piezoelectric transducer at the bottom of said sample cup;
        iv. administering a noble gas at a constant rate into said sample through said device; and
        v. monitoring temperature in said molten iron of said sample in said sample cup, and monitoring vibrations in said molten iron of said sample in said sample cup by taking note of signals from said transducer; and (c) comparing said surface tension as determined with surface tensions of respective previously studied batches of molten iron which solidified to produce respective different forms of cast iron.

2. The method of claim 1, further comprising:

using as said sample cup, a sample cup made of steel.

3. The method of claim 1, wherein:

said positioning is constituted by contacting said transducer to said sample cup for less than one minute.

4. The method of claim 1, wherein:

said positioning is constituted by contacting said transducer to said sample cup for less than 15 seconds.

5. The method of claim 1, wherein:

said administering comprises adjusting flow of said noble gas from a tip of said device such that said noble gas bubbles into said sample at such a rate that at any time only one bubble of noble gas is present in said sample.

6. A method for producing molten iron containing at least one of graphic shape-modifiers and inoculants, to provide molten iron which is capable of solidifying as cast iron having a pre-selected form, comprising the steps of:

(a) taking a sample from the batch of molten iron;

(b) determining the surface tension of said sample, by:
i. adding said sample to a sample cup which has a bottom;
vi. submerging into said sample in said sample cup a device for introducing a noble gas into the molten iron of said sample;
vii. positioning a piezoelectric transducer at the bottom of said sample cup;
viii. administering a noble gas at a constant rate into said sample through said device; and
ix. monitoring temperature in said molten iron of said sample in said sample cup, and monitoring vibrations in said molten iron of said sample in said sample cup by taking note of signals from said transducer; and (c) comparing said surface tension as determined with surface tensions of respective previously studied batches of molten iron which solidified to produce respective different forms of cast iron;

(d) upon determining as a result of said comparing that the surface tension of said sample deviates from the surface tension of a respective said previously studied batch by more than a predetermined threshold amount, modifying presence of at least one of the graphite shape modifiers and inoculants in said batch of molten iron of step (a), iron of said sample in said sample cup, and monitoring vibrations in said molten iron of said sample in said sample cup by taking note of signals from said transducer in such a sense as to shift the surface tension of said batch of molten iron of step (a) towards that of the respective said previously studied batch, to thereby produce a corrected batch of molten iron; and (e) after conducting step (d), releasing said corrected batch of molten iron for casting into molds.

* * * * *